United States Patent [19]

Hunt

[11] 4,026,025

[45] May 31, 1977

[54] DENTAL SYRINGE

[76] Inventor: Roderick S. Hunt, 13888 SW. Shireva Drive, Lake Oswego, Oreg. 97034

[22] Filed: Oct. 28, 1975

[21] Appl. No.: 626,111

[52] U.S. Cl. .................................................. 32/22
[51] Int. Cl.² ....................................... A61C 19/02
[58] Field of Search ................. 32/22, 28; 128/240, 128/241; 242/107.6

[56] References Cited

UNITED STATES PATENTS

| | | | |
|---|---|---|---|
| 3,445,934 | 5/1969 | Harris | 32/22 |
| 3,488,849 | 1/1970 | Lieb et al. | 32/22 |
| 3,593,423 | 7/1971 | Jones | 32/22 |
| 3,698,088 | 10/1972 | Austin, Jr. | 32/22 |
| 3,874,083 | 4/1975 | Buckley | 32/22 |
| 3,889,675 | 6/1975 | Stewart | 128/240 |

Primary Examiner—G.E. McNeill
Attorney, Agent, or Firm—Chernoff & Vilhauer

[57] ABSTRACT

An improved dental syringe for injecting pressurized warm water and air into the oral cavity of a dental patient. A syringe, having an elongate tip for guiding water and air under pressure into a patient's oral cavity and atomizing the water with the air, a body to which the tip is attached including pushbutton controls for regulating the water and air, and a source of pressurized water and air, is provided with a novel flexible, disposable sanitary tip of unitary construction, and the tip is attached to the body by a new, rapidly-operated mechanism which permits the tip to be removed merely by rotating a fastener approximately one half-turn and pulling the tip away from the body, and to be similarly attached by reversing the procedure. The invention also provides a simplified, easily removed three-piece pushbutton control mechanism for regulating the water and air, and a novel flexible conduit leading from the source of water and air to the syringe body, the conduit having a heating element adjacent water and air channels therein for heating the fluids to prevent any significant time delay from actuation of the syringe to arrival of warm fluid at the patient end of the tip.

9 Claims, 11 Drawing Figures

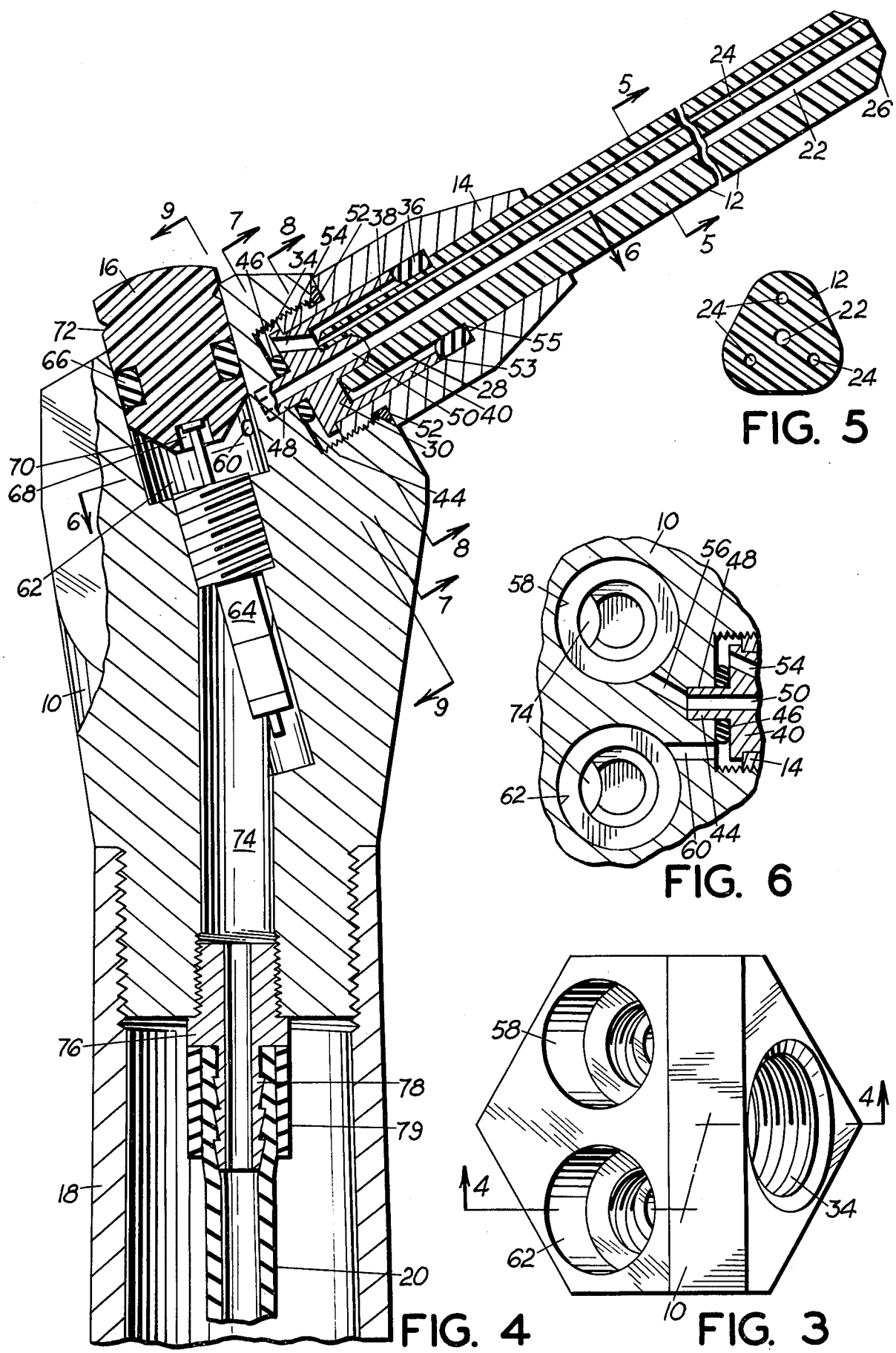

DENTAL SYRINGE

BACKGROUND OF THE INVENTION

This invention relates to dental syringes for injecting warm water and air into the mouth of a dental patient and atomizing the water with the air.

In the dentistry profession it is often necessary while treating a patient to clear the work area within the patient's mouth of waste material utilizing a syringe which produces a controlled spray of pressurized water of air, or both simultaneously such that the air atomizes the water. A conventional syringe for performing the aforementioned function comprises a body, or head, having a handle attached at the bottom thereof and an elongate tip attached to the head for insertion into the oral cavity of the patient to guide the water and air therein. In some cases such a syringe is designed only to provide either water or air, but not both, and in such cases there ordinarily is a single button on the top of the body for actuating the stream of fluid. Syringes providing both water and air ordinarily include two separate buttons adjacent one another on top of the body which may be pressed alternatively either to actuate the water or the air, or they may be pressed simultaneously to actuate both fluids and produce atomization of the water. A flexible supply conduit attached at one end to the head for conducting the fluids thereto is attached at its other end to a source of warm water and air.

A tip for a conventional syringe which supplies both water and air utilizes a multiple-piece metal assembly which is soldered together. Such an assembly typically comprises a large pipe and a small pipe concentrically disposed within the larger pipe, an exit manifold attached to both pipes at the patient end of the tip and a combination entry manifold and collet member attached to the pipes at the head end of the tip such that the two manifolds hold the pipes in position relative to one another thereby permitting water to flow through the center pipe and air through the passage between the center and the outer pipe. The exit manifold is typically provided with several outer, air exit holes disposed around a center, water exit hole and a 45° front chamfer which places the air holes behind the water hole so that the air may expand and strike the water as soon as it exits for effective atomization. Also, the tip assembly is bent a slight, predetermined amount for ease of access to the work area within the oral cavity.

The conventional tip assembly is attached to the syringe head by placing it through a nut which threads into the head and tightens on the collet; consequently, the nut must be completely unscrewed to remove the tip. Additional drawbacks of such a conventional tip are that due to the labor and materials involved in manufacturing such a metal tip it must be sterilized and reused as it is too expensive economically to discard, and the metal of which it is made prevents it from being reshaped without impairing its proper functioning as a guide for the water and air.

The pushbuttons mounted on a conventional syringe head for controlling the fluid emitted by the syringe typically comprise multiple-piece assemblies having a button body, a button stem, a snap ring, a diaphram and a valve mechanism. Such pushbutton assemblies must be removed with the aid of a screwdriver or a special tool and the use of many separate parts tends to increase the cost of production and the difficulty of repair.

The water and air supplied by a conventional syringe are heated at their source to avoid discomfort to the patient. In dual syringes the supply conduit utilizes two adjacent tubes attached to the source, one for carrying water and the other for carrying air. Of course, where a single function syringe is utilized only one tube is needed. The tubes are attached through the handle of the syringe to the body by barbed nipples which are permanently attached to the body, at least in the case of dual syringes. A major drawback of this heating arrangement is that the fluids in the conduit cool off between uses which causes a delay between the time that the syringe is actuated to produce an immediate spray and the arrival of warm fluids, thereby resulting in the initial injection of cold fluids into the oral cavity of the patient which produces considerable discomfort.

SUMMARY OF THE INVENTION

The present invention is directed to an improved dental syringe which overcomes the aforementioned drawbacks of conventional dental syringes by providing a disposable, flexible tip, a mechanism for more quickly and easily attaching the tip to the head of the syringe and for releasing the same, a simpler fluid control mechanism, and a supply cord and fluid source system that virtually delay between the time of actuation of the syringe and the arrival of warm fluid at the patient end of the tip.

To provide a disposable tip the present invention utilizes a flexible material having a central passage for conducting water and a plurality of outer passages, ordinarily three, surrounding the central passage in a symmetrical pattern, resulting in an elongate tip of unitary construction. Such a tip may be inexpensively manufactured from plastic which may be easily bent by hand without any special tools or heating and without impairing its functioning as a fluid guide. Aside from its bendable characteristic the novel tip is particularly advantageous in that it eliminates the need for sterilization of a permanent tip which reduces the time required for preparing equipment, and it eliminates the need for investment in a large number of expensive permanent tips. Also, the tip may be manufactured in virtually any length desired without the need for any special jigs or other equipment.

Rapid attachment and removal of the tip is accomplished by a mounting mechanism which utilizes a separate collet disposed within an aperture in the head of the syringe for accepting the head end of the tip, and a flexible O-ring placed over the head end of the tip for gripping the tip. A nut, similar to a conventional syringe-tip nut having a hole in its center for receiving the tip, is screwed into the aperture to secure the tip by pressing the O-ring against the collet which reduces the opening of the O-ring, causing it to grip the tip. Thus the tip may be quickly released merely by turning the nut approximately one half-turn and pulling the tip out through the center of the nut, and similarly may be attached by reversing this process, thereby considerably reducing the time for tip removal in comparison to the conventional syringe wherein the nut must be entirely removed prior to removal of the tip.

The ease of removal of the control buttons is improved and the expense of their manufacture and maintenance is reduced by a relatively uncomplicated novel pushbutton control mechanism of the present invention. In this mechanism only three pieces, a valve mechanism, a unitary pushbutton and a flexible O-ring placed over the pushbutton to seal the control assembly and provide friction to retain the button, are utilized.

In the present invention heating of the fluids is produced, or augmented, by a heating element, such as an electric wire, which is placed adjacent the tubes of the supply conduit throughout its length. This arrangement is especially advantageous in that it virtually eliminates the delay between actuation of the syringe and arrival of the heated fluid at the patient end of the tip, thereby avoiding considerable discomfort to the patient.

It is therefore a principal objective of this invention to provide a novel and improved dental syringe apparatus having an elongate tip for injection of fluids into the oral cavity of a dental patient.

It is a further objective of the present invention to eliminate the need for repeated sterilization of the tip of a dental syringe and to enable the tip to be more quickly attached and released.

It is another objective of the present invention to provide a dental syringe having a fluid control mechanism wherein the problems in manufacturing and maintaining the control mechanism are reduced.

It is yet another objective of the present invention to provide a dental syringe wherein there is virtually no delay between the time of actuation of the fluid spray and the time of arrival of warm fluid at the patient end of the syringe tip.

It is a principal feature of the present invention that it utilizes a dental syringe having a flexible, disposable tip and an associated rapidly-operated tip-mounting mechanism.

It is another feature of the present invention that it provides a fluid control mechanism utilizing only three easily-removable components.

It is a further feature of the present invention that, in order to provide warm water and air for injection into the patient's oral cavity, it utilizes a heating element adjoining the water and air tubes of a supply conduit, running throughout its length from a source of fluids to the head of the syringe.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 3 is a top view of the head portion of the aforementioned dental syringe taken along line 3—3 of FIG. 1, with fittings removed.

FIG. 4 is a side section of the aforementioned dental syringe taken along line 4—4 of FIG. 3.

FIG. 5 is a section of the preferred embodiment of a novel tip for use in the aforementioned improved dental syringe, taken along line 5—5 of FIG. 4.

FIG. 6 is a top section of the aforementioned dental syringe taken along line 6—6 of FIG. 4, with fittings removed.

DETAILED DESCRIPTION OF THE INVENTION

Figure 1:
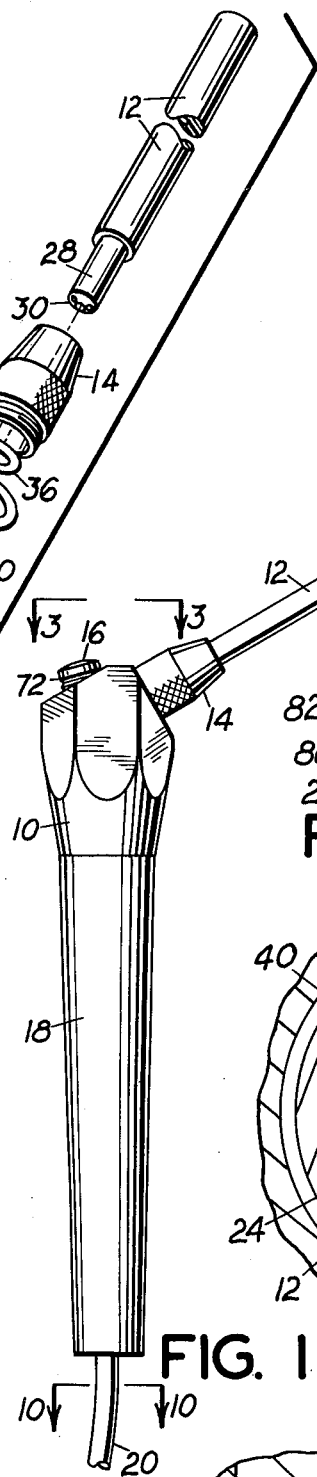
FIG. 1 is a side elevation of the preferred embodiment of the improved dental syringe of the present invention, showing the tip thereof in a moved position.
Figure 7:
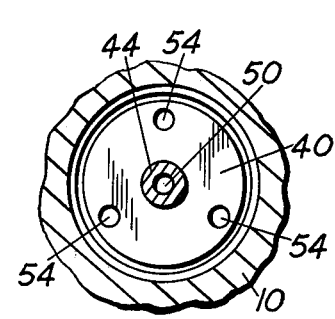
FIG. 7 is a section of the aforementioned dental syringe taken along line 7—7 of FIG. 4.

Referring to FIG. 1, both conventional dental syringes and the improved dental syringe of the present invention comprise a hand-held unit having a head, or body, 10, an elongate tip 12 or guiding pressurized fluid into the oral cavity of a dental patient, a fastener such as a nut 14 for attaching the tip to the head, one or more spring-biased pushbuttons 16 mounted in the head for controlling the pressurized fluid, a handle 18 attached to the head for holding the syringe unit and a supply conduit 20 leading to a source of pressurized fluid for supplying the syringe. Such syringe units may be designed for the single purpose of injecting either water or air, or they may be designed to inject both water and air alternatively and simultaneously, and while the description herein applies primarily to the preferred embodiment of the present invention wherein both water and air may be injected, it should be recognized that some of the improvements described apply to single purpose syringes as well. In dual syringes convention dictates that the left-hand pushbutton, see FIG. 2, actuates and regulates the water injected by the syringe, and the right-hand pushbutton actuates and regulates the air injected, and these pushbuttons may be operated such that either water or air may be injected or, by pressing both pushbuttons simultaneously, both water and air will be injected together causing the air to atomize the water. Typically, the syringe is operated by first pressing the air button and thereaffter rolling one's thumb onto the water button as well so that the water is atomized immediately upon exit from the tip; to facilitate such operation the pushbuttons are often provided with slightly rounded surfaces.

Figure 2:
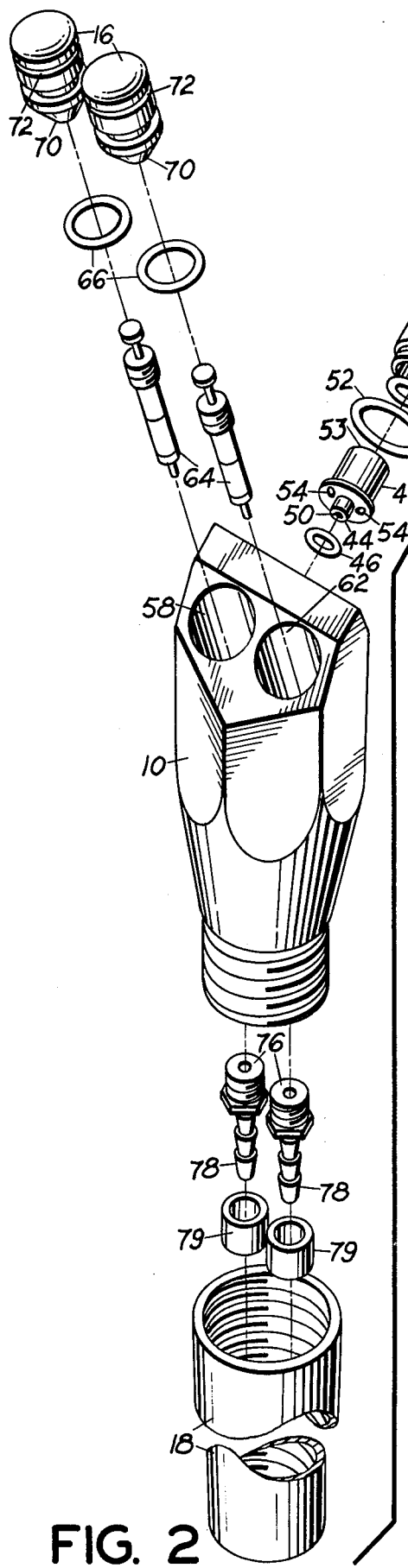
FIG. 2 is an exploded view of the aforementioned improved dental syringe.

Turning now to FIGS. 2, 4 and 5 as well as FIG. 1, the improved dental syringe of the present invention includes a novel tip 12 which may be disposed economically after use, thereby eliminating the need for repeated sterilization. The tip comprises an elongate member of unitary construction having a central passage 22 for conducting water, and a plurality, ordinarily three, of outer passages 24 for conducting air. The patient end of the tip has an approximately 45° chamfer 26, for placing the exit holes of the air channels slightly behind the exit hole of the water channel to facilitate atomization of the water by permitting the air to expand into the water stream close to the water exit hole, and the head end of the tip has a reduced diameter portion 28 for mounting the tip on the head and another 45° chamfer 30 to provide a space for coupling of the tip air channels with air source. Although the reduced diameter portion of the tip has a circular cross section to facilitate mounting of the tip, the larger diameter portion has a semi-triangular cross section, as shown in FIG. 5, which provides the walls adjacent the outer air passages with sufficient strength, while minimizing the material needed for manufacture of the tip. Thus, the tip may be inexpensively fabricated by extruding material having the cross section shown in FIG. 5, cutting it to any desired length and machining the ends of the cut pieces to provide the chamfers and reduced diameter portion, using a conventional automatic screw machine. Plastic materials, such as polyvinyl chloride are particularly suitable for making the tips, and an especially significant advantage of using such a material is that the tips may be bent, as shown by the moved position 32 in FIG. 1, by hand without the aid of special tools or heating equipment and without pinching off the fluid passages therein.

Mounting of the tip is best illustrated with reference to FIGS. 2–4 which shown that the end of the tip is disposed within a mounting aperture 34 formed in the head 10. Mounting is accomplished by placing the head end of the tip through a central hole in the nut 14, then placing the reduced diameter portion 28 through a relatively-tight grasping O-ring 36 and into a cup 38 of a combination collet-manifold member 40, all of which is disposed within the mounting aperture 34. The collet 40 includes a forwardly directed nipple 42 for placement within the head end of the central passage 22 of the tip 12, which is counter bored for receiving the aforementioned nipple, thereby positioning the tip and sealing the central passage off from the outer passages. The collet also has a rearwardly facing nipple 44 placed through a rear O-ring 46 and seated in a hollow 48. A central channel 50 through the collet guides water from a passage in the hollow 48 into the central passage 22 of the tip 12, and the rearwardly facing nipple 44 properly positions the channel 50 and, in conjunction with the O-ring 46, seals off the central channel 50.

The aperture 34 and nut 14 have mating threads so that the nut will screw into the aperture, and a nut O-ring 52 is placed over the threads of the nut for cushioning the joint between the nut and the head 10, and sealing the aperture. When the nut is screwed into the head the grasping O-ring 36 is disposed between the forward end 52 of the collet 40 and a wall 55 formed by an inward jog on the interior of the nut and an outward jog resulting from the reduced diameter portion 28 of the tip. Thus, as the nut is tightened the O-ring 52 is compressed and consequently exerts inward pressure against the tip to hold it in place. Also, the compression of the O-ring 52 seals off any space between the outside of the tip and the inside of the center hole of the nut. This novel mounting mechanism enables the tip to be attached to the head by unscrewing the nut approximately one half-turn, placing the head end of the tip through the center hole and over the forward nipple 42 of the collet and thereafter tightening the nut. Similarly the tip may be removed simply by loosening the nut one half-turn and pulling the tip away from the head.

In a dual syringe, i.e. one for injecting both water and air, water flows through the central channel 50 of the collet into the central passage 22 of the tip, and air must be supplied to the outer passage 24 of the tip. Accordingly, the collet is provided with one or more of outer passages 54 placed through the rear of the collet. While three such passages are shown it should be recognized that other numbers might be used and it is not necessary that these passages correspond in number or position with the passages in the tip, since an air space is formed inside the cup 38 of the collet into which the outer passages of the tip enter, due to the rear chamfer 30 of the tip.

Figure 9:
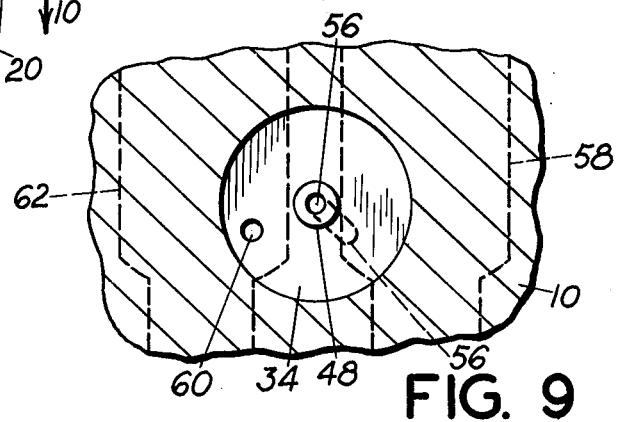
FIG. 9 is a section of the aforementioned dental syringe taken along line 9—9 of FIG. 4.

Since, by convention, the left-hand pushbutton controls the water and the right-hand pushbutton controls the air, the head 10 is provided within an interior passage 56 to a left-hand receptacle 58 for guiding water, and an interior passage 60 to a right-hand receptacle 62 for guiding air, as shown in FIGS. 6 and 9.

As shown in FIGS. 2 and 4, each of the pushbutton controls utilizes only three-parts, that is, a valve mechanism 64 spring-biased closed (a conventional pneumatic tire valve is quite suitable), a monolithic button 16 for actuating the valve and a resilient O-ring 66 placed in a slot around the button. In addition to the slot for receiving the O-ring 66, the button includes a depression 68 for receiving the stem of the valve, a chamfered interior edge 70 for guiding each button into its respective receptacle and forming a fluid passage from each valve to its respective interior passage of the head when the button is depressed, and an exterior groove 72 formed peripherally around the top of the button for grasping the button to remove it. The button is easily installed by simply pushing it into its receptacle, and it is almost as easily removed by simply grasping it using the groove 72 and pulling it out. The O-ring 66 tends to provide optimum resistance against outward movement of the button so that the button will not fall out and it seals off the receptacle so that the fluids therein will not escape around the wall of the button when it is depressed.

Each control valve 64 is threaded into a feed passage 74 which is supplied by water or air, as is appropriate, from the supply conduit 20. A removable barbed nipple 76 which may be replaced if damage is screwed into the opposite end of the passage 74 for receiving the supply conduit. In contrast, conventional syringe units typically utilize nipples soldered directly to the head. Each nipple 76 includes one-way ridges 78 for receiving a portion of the supply conduit 20 and resisting its removal, as is commonly known to the art, and ferrules 79 are placed over the water and air portions of the supply conduit to secure the conduit to the nipples.

Figures 10, 11:
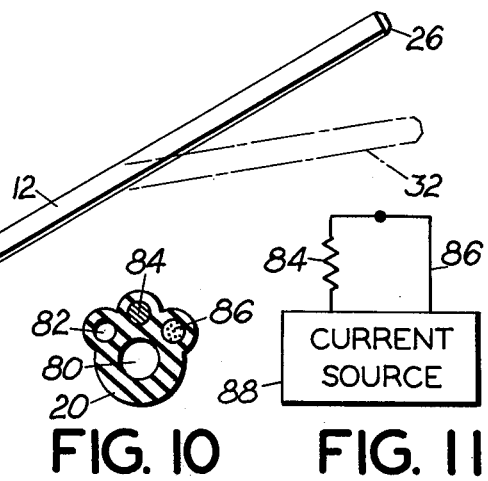
FIG. 10 is a section of the preferred embodiment of a novel supply conduit for use in the aforementioned improved dental syringe, taken along line 10—10 of FIG. 1.
FIG. 11 is a schematic diagram of an exemplary electrical heating circuit for use in the aforementioned improved dental syringe.
Figure 8:
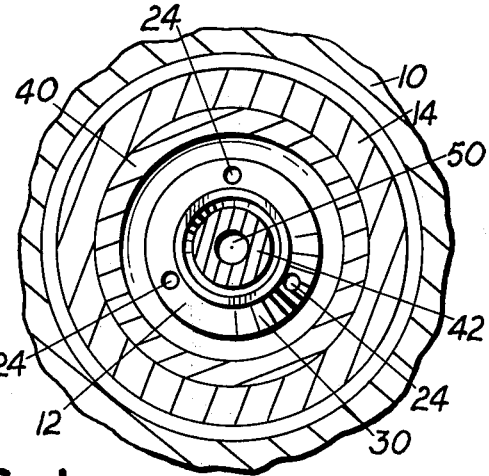
FIG. 8 is a section of the aforementioned dental syringe taken along line 8—8 of FIG. 4.

With reference to FIGS. 10 and 11 an improved supply conduit 20 is provided, having a relatively large passage 80 for conducting water from a pressurized source and a relatively smaller passage 82 for conducting air from a pressurized source. In addition, an electric heating element 84 comprising a high-resistance wire runs throughout the length of the conduit adjacent both the air and water passages for heating the fluids therein to prevent any significant time delay between actuation of the syringe and arrival of warm fluid at the patient end of the tip. A flexible, low-resistance wire 86 is provided as a return path for the current through the high-resistance wire, and both of these wires are connected to an appropriate current source 88 which may include such features as a variable current control and a temperature cut-off switch for preventing the resistance wire from becoming so hot that it might melt the conduit or injure the user. Such a conduit may be manufactured in any of a number of configurations but the one shown is preferred as it is readily adaptable to unitary construction by extrusion of plastic material. It is recognized that other types of heating elements might be utilized without departing from the principles of this invention, and that the afore-described novel supply conduit may be used either alone or in combination with other fluid heating apparatus.

The terms and expressions which have been employed in the foregoing abstract and specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. In a dental syringe for selectively injecting water and air into the oral cavity of a dental patient, said syringe having an elongate tip for guiding the water and air into said oral cavity, means for supporting said tip and means for supplying said tip with controlled amounts of pressurized water and air, the improvement wherein said tip comprises an elongate, flexible member of unitary construction for guiding both said water and said air along separate paths into said oral cavity, said tip having means defining a central longitudinal passage for guiding said water and means defining a plurality of longitudinal air passages surrounding said water passage for guiding said air.

2. The dental syringe of claim 1 wherein said tip is made of a plastic material.

3. The dental syringe of claim 1 wherein said tip is attached to said supporting means by a concentric, rotatable fastener through which an end of said tip is placed and said syringe further includes mounting means associated with said fastener for permitting said tip to be removed from said syringe by rotating said fastener without removal thereof from said supporting means.

4. The syringe of claim 3 wherein said supporting means includes an aperture for receiving said mounting means and fastener, and said mounting means comprises a cup-shaped collet disposed within said aperture for receiving said end of said tip therein, a flexible O-ring surrounding said tip and means for compressing said O-ring against the opening rim of said collet and against said tip in response to the rotation of said fastener to secure said end of said tip within said aperture.

5. The syringe of claim 4 wherein said attached end of said tip is chamfered to form a space between said end of said tip and the interior walls of said collet, said collet having a rear end with a centrally disposed, inwardly directed nipple having a hollow passage therethrough for insertion into said central passage of said tip to guide water therein, and an off-center aperture therethrough for guiding air into said space formed between said tip and the interior walls of said collet.

6. In a dental syringe for selectively injecting fluid into the oral cavity of a dental patient, said syringe having an elongate tip for guiding the fluid into said oral cavity, a hand-held body member for supporting said tip, source means for providing pressurized fluid and flexible, elongate conduit means for conducting said fluid from said source means to said body member, the improvement wherein said conduit means further comprises a passage for conducting said fluid and an elongate electric heating element disposed within said conduit means adjacent said passage substantially throughout the length of said conduit means for heating said fluid while inside said passage.

7. The syringe of claim 6 wherein said source means provides both water and air, said conduit means includes separate adjacent passages for conducting both said water and said air respectively, and said heating element is disposed adjacent both said water and air passages and parallel thereto for heating said water and said air respectively therein.

8. In a dental syringe for selectively injecting fluid into the oral cavity of a dental patient, said syringe having an elongate tip for guiding said fluid into said oral cavity, means for supporting said tip, means for supplying said tip with said fluid, and means for controlling the amount of said fluid supplied to said tip, the improvement wherein said controlling means comprises an aperture formed in said supporting means, a valve disposed within said aperture and spring-biased closed, a monolithic button partially disposed within said aperture for actuating said valve, said button having a partially exposed exterior groove formed around the periphery adjacent an exterior end thereof for removal of said button from said aperture and a slot formed around the periphery between said groove and an interior end thereof for receiving an O-ring, and a resilient O-ring placed around said button within said aperture to seal said aperture and hold said button therein.

9. The syringe of claim 8 wherein said interior end of said button is chamfered to form a space between said button and the interior walls of said aperture and to facilitate insertion of said button in said aperture.

* * * * *

UNITED STATES PATENT AND TRADEMARK OFFICE
CERTIFICATE OF CORRECTION

PATENT NO. : 4,026,025
DATED : May 31, 1977
INVENTOR(S) : Roderick S. Hunt

It is certified that error appears in the above-identified patent and that said Letters Patent are hereby corrected as shown below:

| | |
|---|---|
| Col. 1, Line 12 | Change "of" to --or--. |
| Col. 2, Line 28 | After "virtually" add the word --eliminates--. |
| Col. 4, Line 17 | Change "or" to --for--. |
| Col. 6, Line 32 | Change "damage" to --damaged--. |

Signed and Sealed this

Third Day of January 1978

[SEAL]

Attest:

RUTH C. MASON
Attesting Officer

LUTRELLE F. PARKER
Acting Commissioner of Patents and Trademarks